(12) United States Patent
Takeda et al.

(10) Patent No.: US 8,334,400 B2
(45) Date of Patent: Dec. 18, 2012

(54) HYDROXYL COMPOUND AND A COSMETIC COMPRISING THE SAME

(75) Inventors: Kyoichi Takeda, Narita (JP); Yuki Kokeguchi, Narita (JP)

(73) Assignee: Kokyu Alcohol Kogyo Co., Ltd., Narita-shi (JP)

( * ) Notice: Subject to any disclaimer, the term of this patent is extended or adjusted under 35 U.S.C. 154(b) by 388 days.

(21) Appl. No.: 12/653,745

(22) Filed: Dec. 16, 2009

(65) Prior Publication Data

US 2010/0150855 A1    Jun. 17, 2010

Related U.S. Application Data

(60) Provisional application No. 61/204,711, filed on Jan. 9, 2009.

(30) Foreign Application Priority Data

Dec. 16, 2008    (JP) ................ 2008-319716

(51) Int. Cl.
*C07C 69/74* (2006.01)
*A61K 8/18* (2006.01)

(52) U.S. Cl. ........... 560/190; 514/724; 514/785; 424/63

(58) Field of Classification Search .................. 560/190; 514/785; 554/115, 124

See application file for complete search history.

(56) References Cited

U.S. PATENT DOCUMENTS

| 6,242,499 B1 | 6/2001 | Gruning et al. |
| 2006/0204460 A1 | 9/2006 | Takeda et al. |
| 2008/0188569 A1 | 8/2008 | Takeda et al. |

FOREIGN PATENT DOCUMENTS

| JP | 2004-256515 | 9/2004 |
| JP | 2005-089487 | 4/2005 |
| JP | 2005-132729 | 5/2005 |
| JP | 2005-255525 | 9/2005 |
| JP | 2007-119393 | 5/2007 |
| JP | 2007-284371 | 11/2007 |
| JP | 2008-019200 | 3/2008 |

OTHER PUBLICATIONS

Jul. 15, 2005 "Characteristic of newly-developed dimer acid ester." Kokeguchi et al. Fragrance Journal. vol. 33, No. 7. pp. 35-40.
Nov. 15, 2003 "Development of polyglycerol derivatives as new cosmetic oil." Yasunori Noguchi. Fragrance Journal. vol. 11, No. 11. pp. 137-142.

*Primary Examiner* — Sikarl Witherspoon
(74) *Attorney, Agent, or Firm* — Jordan and Hamburg LLP

(57) ABSTRACT

There are provided a novel hydroxyl compound having proper hydroxyl values which exhibits not only excellent moisturizing ability and emollient ability when it is blended in cosmetics, but also, among others, excellent gloss-holding ability, and a cosmetic comprising said hydroxyl compound. A hydroxyl compound obtained by reacting a di- or higher-valent alcohol with a monovalent carboxylic acid to obtain an ester compound, which is then reacted with dimer acid, characterized in that the di- or higher-valent alcohol is diglycerin, and the monovalent carboxylic acid is a carboxylic acid having 5 to 10 carbon atoms, and a molar ratio among diglycerin, the carboxylic acid having 5 to 10 carbon atoms and dimer acid is 1.0:1.5 to 1.6:0.4 to 0.6.

16 Claims, No Drawings

HYDROXYL COMPOUND AND A COSMETIC COMPRISING THE SAME

REFERENCE TO RELATED APPLICATION

This application claims the benefit of the filing date of Provisional Application No. 61/204,711 filed Jan. 9, 2009.

BACKGROUND OF THE INVENTION

The present invention relates to a hydroxyl compound obtained by reacting a di- or higher-valent alcohol with a monovalent carboxylic acid and dimer acid, and a cosmetic comprising said hydroxyl compound.

In the prior art, hydroxyl compounds obtained by reacting a di- or higher-valent alcohol with a monovalent carboxylic acid and dimer acid are known as an oily base used in cosmetics.

For example, in Japanese Patent Application Laid-Open 2004-256,515, there is known an oily base containing an ester (a) which is obtained by esterifying an oligomeric ester which occurs from esterification between dimer acid and a di- or higher-valent alcohol, with a monovalent alcohol and/or a monovalent carboxylic acid, or an ester (b) which is obtained by esterifying an oligomeric ester which occurs from esterification between dimer diol and a di- or higher-valent carboxylic acid, with a monovalent alcohol and/or a monovalent carboxylic acid. In this patent application, there is disclosed a process for the preparation of the ester (a), wherein dimer acid is reacted with a di- or higher-valent alcohol to obtain an oligomeric ester, of which carboxyl groups and/or hydroxyl groups are then esterified with a monovalent alcohol and/or a monovalent carboxylic acid, or wherein dimer acid, a di- or higher-valent alcohol and a monovalent alcohol and/or a monovalent carboxylic acid are esterified at once. There is also disclosed a process for the preparation of the ester (b), wherein dimer diol is reacted with a di- or higher-valent carboxylic acid to obtain an oligomeric ester, of which carboxyl groups and/or hydroxyl groups are then esterified with a monovalent alcohol and/or a monovalent carboxylic acid, or wherein a dimer diol, a di- or higher-valent carboxylic acid and a monovalent alcohol and/or a monovalent carboxylic acid are esterified at once.

Japanese Patent Application Laid-Open 2005-132,729 discloses cosmetics comprising a mixed ester of aliphatic acid obtained via esterification among polyglycerin, dimer acid and saturated aliphatic acid and/or unsaturated aliphatic acid. In Examples 1 and 2, diglycerin, dimer acid and a carboxylic acid are placed in a reactor at once for esterification.

However, the ester compounds obtained in the aforesaid patent applications have very low hydroxyl values and therefore have drawbacks such as poor moisturizing ability, poor emollient ability and poor gloss-holding ability.

In order to overcome these drawbacks, the present inventors provided cosmetics comprising a hydroxyl compound obtained by the reaction of a di- or higher-valent alcohol with a monovalent carboxylic acid and dimer acid, characterized in that the hydroxyl compound is obtained by reacting diglycerin with isostearic acid to obtain an ester compound which is then reacted with dimer acid, wherein a molar ratio among diglycerin, isostearic acid and dimer acid is in the range of 1.0:1.4 to 1.6:0.5 to 0.8 in WO 2006/095,486 (corresponding to US 2008/0188569 A1). This invention can overcome the drawbacks of the ester compounds obtained in the aforesaid patent applications, that is, poor moisturizing ability and poor emollient ability because of the very low hydroxyl values. However, WO 2006/095,486 did not lead to the remedy of the remaining drawback of poor gloss-holding ability, i.e. the intrinsic gloss of the cosmetic is lost when said hydroxyl compound is used in cosmetics.

SUMMARY OF THE INVENTION

The present invention provides a novel hydroxyl compound having proper hydroxyl values which not only exhibits a good moisturizing property and a good emollient property upon blending in cosmetics, but also holds excellent gloss, and a cosmetic comprising said hydroxyl compound.

Three patent documents mentioned above disclose a hydroxyl compound obtained by reacting a di- or higher-valent alcohol with a monovalent carboxylic acid and dimer acid. These inventions intend to obtain a hydroxyl compound which is excellent in safety, stability, gloss, feeling such as oily feeling, water-holding property such as emollient property and moisturizing property, odor, dispersibility of pigments, compatibility when it is used in cosmetics. Most of these properties have been improved by these inventions. However, the present inventors have found that the hydroxyl compound disclosed in these patent documents have a drawback of not holding gloss when used in cosmetics. The inventors have made investigations on reasons why such a drawback occurs, and consequently have found that humidity or moisture causes disappearance of gloss, and especially when the hydroxyl compound is used in lipsticks or lip-glosses, saliva causes disappearance of gloss. After further investigations, the inventors have found that when a di- or higher-valent alcohol is reacted with a monovalent carboxylic acid to obtain an ester compound, and then the ester compound thus obtained is reacted with dimer acid, and when diglycerin is used as the di- or higher-valent alcohol, and a carboxylic acid having 5 to 10 carbon atoms, preferably isononanoic acid is used as the monovalent carboxylic acid, and particularly when the diglycerin is reacted with the carboxylic acid having 5 to 10 carbon atoms and dimer acid at the predetermined molar ratio, the resulting hydroxyl compound has excellent gloss-holding ability, which leads to the present invention.

Thus, the present invention is (1) a hydroxyl compound obtained by reacting a di- or higher-valent alcohol with a monovalent carboxylic acid to obtain an ester compound, which is then reacted with dimer acid, characterized in that the di- or higher-valent alcohol is diglycerin, and the monovalent carboxylic acid is a carboxylic acid having 5 to 10 carbon atoms, and a molar ratio among diglycerin, the carboxylic acid having 5 to 10 carbon atoms and dimer acid is 1.0:1.5 to 1.6:0.4 to 0.6.

As preferred embodiments of the present invention, mention may be made of:

(2) the hydroxyl compound according to the above (1), wherein the monovalent carboxylic acid is a carboxylic acid having 9 to 10 carbon atoms;

(3) the hydroxyl compound according to the above (1), wherein the monovalent carboxylic acid is isononanoic acid;

(4) the hydroxyl compound according to any one of the above embodiments (1) to (3), wherein the molar ratio among diglycerin, the carboxylic acid having 5 to 10 carbon atoms and dimer acid is 1.0:1.5 to 1.6:0.5 to 0.6;

(5) the hydroxyl compound according to any one of the above embodiments (1) to (4), wherein a hydroxyl value of the hydroxyl compound is in a range of 90 to 160;

(6) the hydroxyl compound according to any one of the above embodiments (1) to (4), wherein a hydroxyl value of the hydroxyl compound is in a range of 100 to 150;

(7) the hydroxyl compound according to any one of the above embodiments (1) to (6), wherein a viscosity at 60 degrees C. of the hydroxyl compound is in a range of 900 to 3,000 Pa·s;

(8) the hydroxyl compound according to any one of the above embodiments (1) to (6), wherein a viscosity at 60 degrees C. of the hydroxyl compound is in a range of 1,000 to 2,600 Pa·s;

(9) the hydroxyl compound according to any one of the above embodiments (1) to (8), wherein a number average molecular weight of the hydroxyl compound is in a range of 700 to 5,000;

(10) the hydroxyl compound according to any one of the above embodiments (1) to (8), wherein a number average molecular weight of the hydroxyl compound is in a range of 720 to 4,400;

(11) the hydroxyl compound according to any one of the above embodiments (1) to (10), wherein water-holding property of the hydroxyl compound is in a range of 30 to 100%;

(12) the hydroxyl compound according to any one of the above embodiments (1) to (10), wherein water-holding property of the hydroxyl compound is in a range of 40 to 90%;

(13) a cosmetic comprising the hydroxyl compound according to any one of the above embodiments (1) to (12);

(14) a cosmetic comprising the hydroxyl compound according to any one of the above embodiments (1) to (12) in an amount of 0.1 to 80% by mass;

(15) a cosmetic comprising the hydroxyl compound according to any one of the above embodiments (1) to (12) in an amount of 0.5 to 70% by mass; and

(16) the cosmetic according to any one of the above embodiments (13) to (15) for hair treatments, foundations, eye shadows, lip glosses or lipsticks.

The hydroxyl compound of the present invention exhibits a particular effect, gloss-holding ability, which has not been attained using the prior art hydroxyl compound. In other words, the hydroxyl compound of the present invention can hold the excellent gloss even if it comes into contact with humidity or moisture in air, or with saliva. In addition, the hydroxyl compound of the present invention has proper hydroxyl values and water-holding property which are comparable to those of the prior art hydroxyl compound, and may exhibit not only excellent oily feeling, moisturizing ability and emollient ability, but also easy applicability, safety to the skin and storage stability when blended in cosmetics.

DETAILED DESCRIPTION OF THE INVENTION

The monovalent carboxylic acid used in the preparation of the hydroxyl compound of the invention is a carboxylic acid having 5 to 10 carbon atoms, preferably a carboxylic acid having 9 to 10 carbon atoms. As the carboxylic acid, mention may be made of pentanoic acid, hexanoic acid, heptanoic acid, octanoic acid, nonanoic acid, decanoic acid, and isomers thereof. Among these, use is preferably made of neopentanoic acid, 2-ethylhexanoic acid, isononanoic acid and neodecanoic acid, more preferably isononanoic acid and neodecanoic acid, and most preferably isononanoic acid. If the number of carbon atoms is below the aforesaid lower limit, odor and safety to the skin are poor and furthermore, water-holding property of the hydroxyl compound is considerably lowered, so that moisturizing ability of the cosmetic comprising the hydroxyl compound decreases. If it exceeds the upper limit, the gloss of the hydroxyl compound considerably decreases when it contacts with water, so that gloss-holding ability of the cosmetic comprising the hydroxyl compound also considerably decreases.

Diglycerin and dimer acid are all known compounds and commercially available ones may be used. As diglycerin, for instance, use may be made of "diglycerin 801", trademark, from Sakamoto Yakuhin Kogyo Co., Ltd., and "DIGLYCEROL", trademark, from Solvay. As dimer acid, for instance, use may be made of those described in the above mentioned three patent documents. As commercially available ones, mention may be made of, for instance, "PRIPOL 1009", trademark, from Croda, "Empol 1062" and "Empol 1008", trademarks, from Cognis, and "Unidyme 14" and "Unidyme 14R", trademarks, from Arizona Chemical. Here, dimer acid is a cyclic dibasic acid obtained by polymerizing two molecules of unsaturated aliphatic acid, such as oleic acid and linoleic acid, via the Diels-Alder reaction. The aforementioned commercially available dimer acid is one obtained by hydrogenation and subsequent distillation of a Diels-Alder product, and is also referred to as hydrogenated dimer acid.

In the present invention, diglycerin and the carboxylic acid having 5 to 10 carbon atoms are used in a molar ratio of 1.0:1.5 to 1.6. If the ratio of the carboxylic acid having 5 to 10 carbon atoms is out of the above range, the gloss of the hydroxyl compound considerably decreases when it contacts with water. Diglycerin and dimer acid are used in a molar ratio of 1.0:0.4 to 0.6, and preferably 1.0:0.5 to 0.6. If the ratio of the dimer acid is below the aforementioned lower limit, the degree of polymerization of the hydroxyl compound is not enough to result in an oligomer with low viscosity. If the ratio exceeds the aforementioned upper limit, the degree of polymerization of the hydroxyl compound is significantly large to cause gelation in a reactor, so that the reaction may not be completed.

The hydroxyl compound of the present invention may be prepared according to the process described in WO 2006/095, 486. The preparation is conducted in a two-step process comprising a first step wherein diglycerin is reacted with the carboxylic acid having 5 to 10 carbon atoms, and a second step wherein the ester compound thus obtained is then reacted with dimer acid. In the first step, the carboxylic acid having 5 to 10 carbon atoms binds dominantly to the hydroxyl group at position 1, primary hydroxyl group, of the diglycerin due to the reactivity difference among the hydroxyl groups of the diglycerin. Accordingly, there are obtained more mono-esters or di-esters having structures where hydroxyl groups at position 1 of the diglycerin are esterified. Upon further esterification with dimer acid, more hydroxyl compound has a coupled structure wherein the dimer acid binds to the remaining hydroxyl group at position 2, secondary hydroxyl group. With this process, it is possible to control properties of the hydroxyl compound, such as viscosity, number average molecular weight, and hydroxyl value, more properly than with the one-step process wherein diglycerin, a carboxylic acid having 5 to 10 carbon atoms and dimer acid are reacted simultaneously. It is also possible to reduce variation in properties, which occurs among lots of raw materials and types, volumes or structures of a reactor.

An example of the two-step process is as follows: in the first step, diglycerin and a carboxylic acid having 5 to 10 carbon atoms are placed in a reactor and the temperature is raised gradually preferably to a temperature of from 100 to 250 degrees C., and more preferably from 180 to 240 degrees C., while distilling off the produced water. The reaction mixture is retained at the temperature preferably until no water is distilled off any more. The retention time is preferably 2 to 50 hours, more preferably 3 to 40 hours, and further more preferably 4 to 30 hours. In the second step, the ester compound obtained in the first step and dimer acid are placed in a reactor and, then, reacted under the same conditions as in the first step. In the first step, the reaction is performed so that the hydroxyl value of the ester of diglycerin with the carboxylic acid having 5 to 10 carbon atoms is preferably 300 to 500. In actual operation, an acid value of the ester compound is monitored and adjusted preferably to at most 10, more preferably at most 5. The acid value can be determined accurately in a shorter time, compared to the hydroxyl value, so that reaction is controlled more easily with the acid value. The acid value is determined according to the Cosmetics Raw Material Standards. By controlling the hydroxyl or acid value in this way, it is possible to easily control the viscosity and the hydroxyl value of the desired hydroxyl compound in the reaction of the ester compound obtained in the first step with a predetermined amount of dimer acid in the second step.

The reaction described above is performed preferably in the absence of a solvent and a catalyst, whereby it is possible to obtain a hydroxyl compound in a homogenous state in a reproducible manner. The hydroxyl compound obtained is not accompanied with a solvent or catalyst, so that a cosmetic containing the compound is safer to the skin. Meanwhile, a catalyst and/or a solvent may be used, whereby reaction time may be shortened. As examples of the catalyst, mention may be made of sodium hydroxide, para-toluenesulfonic acid, sulfuric acid, hydrochloric acid, methanesulfonic acid, boron trifluoride, and hydrogen fluoride. As examples of the solvent, mention may be made of benzene and toluene.

The upper limit of the hydroxyl value of the obtained hydroxyl compound is preferably 160, more preferably 155 and further more preferably 150, and the lower limit is preferably 90, more preferably 95, and further more preferably 100. If the hydroxyl value exceeds the aforementioned upper limit, the compound is less compatible with oily bases. If the hydroxyl value is lower than the aforementioned lower limit, the compound is poor in the moisturizing property and the emollient property.

The upper limit of the viscosity at 60 degrees C. of the hydroxyl compound is preferably 3,000 mPa·s, more preferably 2,800 mPa·s, and furthermore preferably 2,600 mPa·s. The lower limit is preferably 900 mPa·s, more preferably 950 mPa·s, and further more preferably 1,000 mPa·s. Above the aforementioned upper limit, it is too tacky, so that handling of it is difficult. Below the lower limit, tackiness is too poor for cosmetics.

The upper limit of the number average molecular weight of the hydroxyl compound is preferably 5,000, more preferably 4,700, and further more preferably 4,400. The lower limit is preferably 700, more preferably 710, and further more preferably 720. Above the aforementioned upper limit, handling of it is difficult. Below the lower limit, tackiness is too poor for cosmetics.

The upper limit of water-holding property of the hydroxyl compound is preferably 100%, more preferably 95%, and further more preferably 90%. The lower limit is preferably 30%, more preferably 35%, and further more preferably 40%. Above the aforementioned upper limit, the compound becomes clouded upon contact with water, which causes decrease of gloss. Below the lower limit, the compound is poor in the moisturizing property or the emollient property.

The hydroxyl compound of the present invention can be used in various cosmetics, such as hair treatments, foundations, eye shadows, lipsticks and lip glosses. The content of the hydroxyl compound of the present invention in cosmetics depends on the type of the cosmetics and ranges preferably from 0.1 to 80% by mass, more preferably from 0.5 to 70% by mass, and further more preferably from 0.5 to 60% by mass.

In the following Examples, the present invention will be described in more detail, but not limited thereto.

EXAMPLES

Preparation Examples and Comparative Preparation Examples

The substances used in the Preparation Examples and the Comparative Preparation Examples were as follows, unless otherwise stated;

Diglycerin: "Diglycerin 801", trademark, from Sakamoto Yakuhin Kogyo Co., Ltd.,

Isononanoic acid: "Kyowanoic-N", trademark, from Kyowa Hakko Chemical Co., Ltd., Isostearic acid: "Isostearic acid EX", trademark, from Kokyu Alcohol Kogyo Co., Ltd., Isobutanoic acid (Isobutyric acid): "2-methyl butyric acid", trademark, from Toyo Gosei Co., Ltd., Neopentanoic acid: neopentanoic acid from Exxon Mobile Corporation, 2-Ethylhexanoic acid: octyl acid from Kyowa Hakko Chemical Co., Ltd., Neodecanoic acid: "Neodecanoic acid PG", trademark, from Exxon Mobile Corporation, Lauric acid: "Profac 1299", trademark, from Southern Acid Chemical, and Dimer acid: "PRIPOL 1009, trademark, from CRODA Inc.

Acid value, hydroxyl value, viscosity, number average molecular weight, water-holding property and gloss of the hydroxyl compound obtained in the Preparation Examples and the Comparative Preparation Examples were determined as follows;

Acid value: determined in accordance with "Cosmetics Raw Material Standard 18, Method for the Determination of an Acid Value".

Hydroxyl value: determined in accordance with "Cosmetics Raw Material Standard 24, Method for the Determination of a Hydroxyl Value".

Viscosity: determined by Brookfield Viscometer DV-II+ (Spindle No. 3, 12 rpm, 60 degrees C.).

Number average molecular weight: determined from distribution of molecular weight relative to polystyrene via GPC, gel permeation chromatography, under the following conditions;

Instrument: GPC-101 from Syowa Denko Co., Ltd.,
Column: two Shodex GPC KF-603,
Eluent: THF,
Temperature: 40 degrees C. in a temperature-controlled bath for column,
Flow rate: 0.5 mL/min.,
Injection volume: 100 µL, about 0.2% (weight/volume),
Solubility: completely dissolved,
Detector: Refractive Index Detector (RI).

Water-Holding Property (Moisturizing Ability or Emollient Ability)

Ten grams of the hydroxyl compound at 35 degrees C. was weighed into a container kept at 35 degrees C. and purified water at 35 degrees C. was added dropwise and kneaded until no more water could be mixed in homogeneously. The mixture was kept at 25 degrees C. for 24 hours and then the amount of water that was separated from the mixture was weighed. The water-holding capacity (%) was expressed as a ratio of the weight of the purified water finally contained in the mixture to the weight of the esterified compound at the starting point (10 g), which is referred to as water-holding property.

Intrinsic Gloss of the Hydroxyl Compound

One gram of the hydroxyl compound was applied in a thickness of about 200 μm on an area of about 20 mm in length and about 40 mm width on a sheet of waxed paper. Using a gloss checker IG-330, trademark, from Horiba Ltd., gloss was determined three times at an angle of incidence of 60 degrees and an angle of reflection of 60 degrees. The average value was used as gloss.

Gloss of the Hydroxyl Compound Upon Contact with Water

Upon contact with saliva, the hydroxyl compound becomes clouded and the gloss of the hydroxyl compound decreases, which greatly influences its appearance. In order to evaluate the gloss in appearance, a transmittance of the hydroxyl compound upon contact with water is used as an indicator of gloss. One gram of the hydroxyl compound was applied in a thickness of about 200 μm on an area of about 10 mm in length and about 20 mm in width on a plate made of quartz, after which 0.1 mL of purified water was added dropwise on the hydroxyl compound. After the hydroxyl compound was lightly kneaded with water by fingers five times back and forth, the applied surface was smoothed with a spatula and then a transmittance, T %, was determined with a spectrophotometer for ultraviolet and visible region, UV-160A, trademark, from Shimazu Corporation. The intrinsic transmittance of the hydroxyl compound was represented as 100%, and then the transmittance of that upon contact with water was determined. "Gloss" was evaluated by the difference between both the transmittances.

Preparation Example 1

In a four-neck 1000 mL flask equipped with a stirrer, a thermometer, a gas inlet tube, and a Dean-Stark condenser with a water measuring trap were placed 166.2 g (1.0 mol) of diglycerin, 237.3 g (1.5 mol) of isononanoic acid, and 150 mL of toluene as a solvent. Then, the reaction mixture was heated to 200 degrees C. under a flow of nitrogen gas in a rate of 20 mL/min. At the temperature, the reaction took place while distilling off the produced water with the solvent azeotropically. When the distillation-off water subsided, the temperature was raised to 220 degrees C. to further continue the reaction. When the distillation-off water stopped, the reaction was terminated. It took about 6 hours from the start of the reaction to this point. Diglycerin isononanoate was obtained as a pale yellow viscous oil in an amount of 411.5 g (hydroxyl value: 132, acid value: 0.3).

Next, the above-described apparatus was charged with 370.4 g (0.90 mole) of the obtained diglycerin isononanoate and 252.6 g (0.45 mole) of dimer acid. Then, under a flow of nitrogen gas at a rate of 20 mL/min., the reaction took place while distilling off the produced water at a temperature of 220 degrees C. as described above. When the distillation-off water stopped, the reaction was terminated. It took about 7 hours from the start of the reaction to this point. Then, after the temperature was lowered to 180 degrees C., the pressure was reduced to about 20 mmHg to remove toluene, solvent, completely. Then 566.7 g of the hydroxyl compound was obtained as a pale yellow highly viscous oil.

The molar ratio among diglycerin, isononanoic acid and dimer acid used in the reaction was 1.00:1.50:0.50.

Preparation Example 2

The procedures of Preparation Example 1 were repeated, except that the amount of dimer acid used in the second step was changed to 202.1 g (0.36 mol). 519.8 g of the hydroxyl compound was obtained as a pale yellow highly viscous oil.

The molar ratio among diglycerin, isononanoic acid and dimer acid used in the reaction was 1.00:1.50:0.40.

Preparation Example 3

The procedures of Preparation Example 1 were repeated, except that the amount of dimer acid used in the second step was changed to 277.8 g (0.495 mol). 589.8 g of the hydroxyl compound was obtained as a pale yellow highly viscous oil.

The molar ratio among diglycerin, isononanoic acid and dimer acid used in the reaction was 1.00:1.50:0.55.

Preparation Example 4

The procedures of Preparation Example 1 were repeated, except that the amount of dimer acid used in the second step was changed to 303.2 g (0.54 mol). 613.1 g of the hydroxyl compound was obtained as a pale yellow highly viscous oil.

The molar ratio among diglycerin, isononanoic acid and dimer acid used in the reaction was 1.00:1.50:0.60.

Preparation Example 5

The procedures of Preparation Example 4 were repeated, except that the amount of isononanoic acid used in the first step was changed to 253.1 g (1.60 mol). 602.3 g of the hydroxyl compound was obtained as a pale yellow highly viscous oil.

The molar ratio among diglycerin, isononanoic acid and dimer acid used in the reaction was 1.00:1.60:0.55.

Preparation Example 6

The procedures of Preparation Example 3 were repeated, except that 153.2 g (1.50 mol) of neopentanoic acid was used in place of isononanoic acid in the first step. 515.3 g of the hydroxyl compound was obtained as a pale yellow highly viscous oil.

The molar ratio among diglycerin, neopentanoic acid and dimer acid used in the reaction was 1.00:1.50:0.55.

Preparation Example 7

The procedures of Preparation Example 3 were repeated, except that 216.3 g (1.50 mol) of 2-ethylhexanoic acid was used in place of isononanoic acid in the first step. 569.3 g of the hydroxyl compound was obtained as a pale yellow highly viscous oil.

The molar ratio among diglycerin, 2-ethylhexanoic acid and dimer acid used in the reaction was 1.00:1.50:0.55.

Preparation Example 8

The procedures of Preparation Example 3 were repeated, except that 258.4 g (1.50 mol) of neodecanoic acid was used in place of isononanoic acid in the first step. 608.6 g of the hydroxyl compound was obtained as a pale yellow highly viscous oil.

The molar ratio among diglycerin, neodecanoic acid and dimer acid used in the reaction was 1.00:1.50:0.55.

Comparative Preparation Example 1

The procedures of Preparation Example 3 were repeated, except that the amount of isononanoic acid used in the first step was changed to 221.5 g (1.40 mol). 577.5 g of the hydroxyl compound was obtained as a pale yellow highly viscous oil.

The molar ratio among diglycerin, isononanoic acid and dimer acid used in the reaction was 1.00:1.40:0.55.

Comparative Preparation Example 2

The procedures of Preparation Example 3 were repeated, except that the amount of isononanoic acid used in the first step was changed to 268.9 g (1.7 mol). 614.7 g of the hydroxyl compound was obtained as a pale yellow highly viscous oil.

The molar ratio among diglycerin, isononanoic acid and dimer acid used in the reaction was 1.00:1.70:0.55.

Comparative Preparation Example 3

The procedures of Preparation Example 3 were repeated, except that the amount of dimer acid used in the second step was changed to 176.8 g (0.315 mol). 496.7 g of the hydroxyl compound was obtained as a pale yellow highly viscous oil.

The molar ratio among diglycerin, isononanoic acid and dimer acid used in the reaction was 1.00:1.50:0.35.

Comparative Preparation Example 4

The procedures of Preparation Example 3 were repeated, except that the amount of dimer acid used in the second step was changed to 328.4 g (0.585 mol). However, the reaction products were gelated in the latter part of the reaction in the second step, so that the hydroxyl compound was not able to be obtained.

The molar ratio among diglycerin, isononanoic acid and dimer acid used in the reaction was 1.00:1.50:0.65.

Comparative Preparation Example 5

The procedures of Preparation Example 1 were repeated, except that 426.8 g (1.5 mol) of isostearic acid was used in place of isononanoic acid. 734.6 g of the hydroxyl compound was obtained as a pale yellow highly viscous oil.

The molar ratio among diglycerin, isostearic acid and dimer acid used in the reaction was 1.00:1.50:0.50.

Comparative Preparation Example 6

The procedures of Comparative Preparation Example 5 were repeated, except that the amount of dimer acid used in the second step was changed to 382.4 g (0.585 mol). 804.4 g of the hydroxyl compound was obtained as a pale yellow highly viscous oil.

The molar ratio among diglycerin, isostearic acid and dimer acid used in the reaction was 1.00:1.50:0.65.

Comparative Preparation Example 7

The procedures of Preparation Example 3 were repeated, except that 132.2 g (1.5 mol) of isobutanoic acid, or isobutyric acid, was used in place of isononanoic acid. 496.0 g of the hydroxyl compound was obtained as a pale yellow highly viscous oil.

The molar ratio among diglycerin, isobutanoic acid (isobutyric acid) and dimer acid used in the reaction was 1.00:1.50:0.55.

Comparative Preparation Example 8

The procedures of Preparation Example 3 were repeated, except that 300.5 g (1.5 mol) of lauric acid was used in place of isononanoic acid. 645.8 g of the hydroxyl compound was obtained as a pale yellow highly viscous oil.

The molar ratio among diglycerin, lauric acid and dimer acid used in the reaction was 1.00:1.50:0.55.

Properties of the substances obtained in the Preparation Examples and the Comparative Preparation Examples are shown in Table 1.

TABLE 1

|  | Molar ratio | | | Acid value | Hydroxyl value | Viscosity in mPa·s at 60° C. | Number average molecular weight | Water-holding property in % | Gloss | |
|---|---|---|---|---|---|---|---|---|---|---|
|  | Diglycerin | Isononanoic acid | Dimer acid |  |  |  |  |  | Intrinsic gloss | Gloss upon contact with water |
| Prep. Ex. 1 | 1.00 | 1.50 | 0.50 | 0.3 | 132 | 1470 | 1190 | 74 | 77 | 98 |
| Prep. Ex. 2 | 1.00 | 1.50 | 0.40 | 0.5 | 155 | 1050 | 820 | 82 | 77 | 96 |
| Prep. Ex. 3 | 1.00 | 1.50 | 0.55 | 0.1 | 116 | 1880 | 3720 | 59 | 78 | 99 |
| Prep. Ex. 4 | 1.00 | 1.50 | 0.60 | 0.9 | 106 | 2620 | 4200 | 53 | 77 | 99 |
| Prep. Ex. 5 | 1.00 | 1.60 | 0.55 | 1.6 | 107 | 1750 | 3250 | 50 | 74 | 98 |
| Prep. Ex. 6 | 1.00 | 1.50[*1] | 0.55 | 4.5 | 135 | 2510 | 2780 | 40 | 74 | 94 |
| Prep. Ex. 7 | 1.00 | 1.50[*2] | 0.55 | 0.2 | 126 | 1920 | 3360 | 45 | 74 | 92 |
| Prep. Ex. 8 | 1.00 | 1.50[*3] | 0.55 | 4.8 | 114 | 1560 | 3810 | 62 | 75 | 96 |
| Com. Prep. Ex. 1 | 1.00 | 1.40 | 0.55 | 0.8 | 129 | 1940 | 3640 | 350 | 75 | 65 |
| Com. Prep. Ex. 2 | 1.00 | 1.70 | 0.55 | 1.6 | 107 | 880 | 3250 | 68 | 75 | 90 |
| Com. Prep. Ex. 3 | 1.00 | 1.50 | 0.35 | 0.1 | 180 | 820 | 770 | 70 | 77 | 90 |
| Com. Prep. Ex. 4 | 1.00 | 1.50 | 0.65 | —[*7] | —[*7] | —[*7] | —[*7] | —[*7] | —[*7] | —[*7] |
| Com. Prep. Ex. 5 | 1.00 | 1.50[*4] | 0.50 | 3.5 | 88 | 980 | 3300 | 388 | 78 | 77 |
| Com. Prep. Ex. 6 | 1.00 | 1.50[*4] | 0.65 | 1.6 | 53.5 | 3900 | 4400 | 473 | 79 | 83 |
| Com. Prep. Ex. 7 | 1.00 | 1.50[*5] | 0.55 | 4.2 | 140 | 3120 | 3540 | 22 | 74 | 90 |
| Com. Prep. Ex. 8 | 1.00 | 1.50[*6] | 0.55 | 0.2 | 108 | 3330 | 3930 | 112 | 75 | 80 |

In Table 1,
[*1] Neopentanoic acid was used in place of isononanoic acid.
[*2] 2-ethylhexanoic acid was used in place of isononanoic acid.
[*3] Neodecanoic acid was use in place of isononanoic acid.
[*4] Isostearic acid was used in place of isononanoic acid.
[*5] Isobutanoic acid (isobutyric acid) was used in place of isononanoic acid.
[*6] Lauric acid was used in place of isononanoic acid.
[*7] Gelation occurred during the reaction, so that the hydroxyl compound was not able to be obtained.

The molar ratio of dimer acid is varied within the present invention in Preparation Examples 1 to 4. The hydroxyl compounds obtained are good in gloss, and in addition, the decrease of gloss is considerably low upon contact with water. In Preparation Example 5, the molar ratio of isononanoic acid is changed in comparison to that in Preparation Example 3. The hydroxyl compound obtained was good in gloss as in the above Preparation Examples. Accordingly, when the hydroxyl compound is used, for instance, in cosmetics, the gloss will not decrease upon contact with water in air or with saliva. In Preparation Example 6, neopentanoic acid having five carbon atoms is used in place of isononanoic acid, and in Preparation Example 7, 2-ethylhexanoic acid having eight carbon atoms is, used in place of isononanoic acid. In either case, the effects of the present invention was sufficiently demonstrated, although the gloss somewhat decreased, compared to one using isononanoic acid.

Meanwhile, in Comparative Preparation Examples 1 and 2, the molar ratio of isononanoic acid is out of the range of the present invention, in comparison to Preparation Example 3. In either case, the gloss considerably decreased upon contact with water. In Comparative Preparation Examples 3 and 4, the molar ratio of dimer acid is out of the range of the present invention, in comparison to Preparation Example 3. In Comparative Preparation Examples 3, the gloss considerably decreased upon contact with water as the above cases, and the product was poor in viscosity. In Comparative Preparation Example 4, the reaction product gelated during the reaction with dimer acid, so that the hydroxyl compound was not able to be obtained. In Comparative Preparation Examples 5 to 8, in either case, use was made of a monovalent carboxylic acid of which number of carbon atoms was out of the range of the present invention. In all the cases, the gloss considerably decreased upon contact with water. Moreover, the hydroxyl compound obtained in Comparative Preparation Examples 7 has problems in odor and in safety to the skin.

Examples and Comparative Examples

The substances used in the following Examples and Comparative Examples are as follows, unless otherwise stated:
Component (A):
Dipentaerythrityl hexa (hydroxystearate/stearate/rosinate): from Kokyu Alcohol Kogyo Co., Ltd., HAILUCENT 138DP, trademark
(Polyglyceryl-2 isostearate/dimer dilinoleic acid) copolymer: from Kokyu Alcohol Kogyo Co., Ltd., HAILUCENT ISDA, trademark
Bis-ethoxydiglycol succinate: from Kokyu Alcohol Kogyo Co., Ltd., HAIAQUEOUSTER, trademark
Neopentylglycol diisononanoate: from Kokyu Alcohol Kogyo Co., Ltd., NPDIN
Isopropyl palmitate: from Kokyu Alcohol Kogyo Co., Ltd., IPP
Jojoba oil: from Kokyu Alcohol Kogyo Co., Ltd., ECOOIL RS, trademark
Macadamia nut oil: from Nikko Chemicals Co., Ltd., NIKKOL Macadamian nut oil, trademark
Stearyl alcohol: from Kokyu Alcohol Kogyo Co., Ltd., STEARYL ALCOHOL NX, trademark
Cetostearyl alcohol: from Kokyu Alcohol Kogyo Co., Ltd., CETANOL NX, trademark
Behenyl alcohol: from Kokyu Alcohol Kogyo Co., Ltd., BEHENYL ALCOHOL 65, trademark
Dipropylene glycol: from Kuraray Co., Ltd., DPG-RF, trademark
Stearyl trimonium chloride: from Clariant, Genamin STAC, trademark
Distearyl dimonium chloride: from Clariant, Genamin DSAC, trademark
Behen trimonium chloride: from Clariant, Genamin KDM-P, trademark
Dicoco dimonium chloride: from Takemoto Oil & Fat Co., Ltd., Pionin B-2211, trademark
Amodimethicone: from Dow Corning Toray Co., Ltd., SF 8452 C, trademark
Cyclomethicone: from Dow Corning Toray Co., Ltd., SH245 Fluid, trademark
Dimethicone: from GE Toshiba Silicone Co., Ltd., TSF451-100A, trademark, used in Examples 1 to 3
Dimethicone: from Momentive Performance Materials Japan Co., Ltd., TSF451-10A, trademark, used in Examples 4 to 6
Phenoxy ethanol: from Toho Chemical Industry Co., Ltd., Hisolve EPH, trademark
Hexyldecyl isostearate: from Kokyu Alcohol Kogyo Co. Ltd., ICIS
Neopentyl glycol diethylhexanoate: from Kokyu Alcohol Kogyo Co., Ltd., KAK NDO, trademark
Squalane: from Kokyu Alcohol Kogyo Co., Ltd., OLIVE SQUALANE
(Diglycerin/dilinoleic acid/hydroxystearic acid) copolymer: from Kokyu Alcohol Kogyo Co., Ltd., RISOCAST HSDA, trademark
Sorbitan monoisostearate: from Nihon Emulsion Co., Ltd., EMALEX SPIS-100, trademark, used in Examples 4 to 6
Sorbitan monoisostearate: from Nihon Emulsion Co., Ltd., EMALEX SPIS-150, trademark, used in Examples 7 to 8
Dimethicone copolyol: from Evonik Goldschmidt GmbH, ABIL EM90, trademark
Pentylene glycol: from Kokyu Alcohol Kogyo Co., Ltd., DIOL PD, trademark
Cetanol: from Kokyu Alcohol Kogyo Co., Ltd., Cetanol NX, trademark
Hydrogenated rapeseed oil alcohol: from Kokyu Alcohol Kogyo Co., Ltd., ALCOHOL No. 20-B, trademark
Dextrin palmitate: from Chiba Flour Milling Co., Ltd., Rheopearl TT2, trademark, used in Examples 4 to 6
Dextrin palmitate: from Chiba Flour Milling Co., Ltd., Rheopearl KL2, trademark, used in Examples 7 to 8
Microcrystalline wax: from Nikko Rica Corporation, Microcrystalline wax
Hydrophobicated titanium oxide: from US Cosmetic Corporation, NHS-TRI-77891, trademark
Hydrophobicated iron oxide yellow: from US Cosmetic Corporation, NHS-Y-77492, trademark
Hydrophobicated iron oxide red: from US Cosmetic Corporation, NHS-R-77491, trademark
Hydrophobicated iron oxide black: from US Cosmetic Corporation, NHS-B-77499, trademark
Talc: from US Cosmetic Corporation, Soft Talc, trademark
Ethylhexyl methoxycinnamate: from ISP Corporation, ESCALOL 557, trademark
Nylon-6: from Ube Industries, Ltd., POMP605, trademark
Crosslinked type silicone powder: from Dow Corning Toray Co., Ltd., Torefil E506C, trademark
Isostearyl isostearate: from Kokyu Alcohol Kogyo Co., Ltd., ISIS
Triethylhexanoin: from Kokyu Alcohol Kogyo Co., Ltd., TOG
Mineral oil: from Kaneda Co., Ltd., HICALL K230, trademark Diisostearyl malate: from Kokyu Alcohol Kogyo Co., Ltd., HAIMALATE DIS, trademark Glyceryl stearate (SE): from Nihon Emulsion Co., Ltd., EMALEX GMS-195, trademark Polyglyceryl-10 stearate: from Nikko Chemicals Co., Ltd., NIKKOL Decaglyn 1-SV, trademark Hydrophobicated ultramarine: from Whittaker Clark & Daniels Inc., 7104 Ultramarine Blue, trademark $TiO_2$ coated mica: from Merk & Co., Inc., Timiron Star Luster MP-115, trademark Hydrogenated polyisobutene: from NOF Corporation, PARLEAM18, trademark Hydrogenated castor oil dimer-dilinoleate: from Kokyu Alcohol Kogyo Co., Ltd., RISOCAST DA-H, trademark, used in Examples 9 to 14

Hydrogenated castor oil dimer-dilinoleate: from Kokyu Alcohol Kogyo Co., Ltd., RISOCAST DA-L, trademark, used in Examples 15 to 18

Polyglyceryl-2 diisostearate: from Kokyu Alcohol Kogyo Co., Ltd., RISOREX PGIS22, trademark Polyglyceryl-2 triisostearate: from Kokyu Alcohol Kogyo Co., Ltd., RISOREX PGIS23, trademark Pentaerythrityl tetraisostearate: from Kokyu Alcohol Kogyo Co., Ltd., KAK PTI, trademark Ethylhexyl hydroxystearate: from Kokyu Alcohol Kogyo Co. Ltd., RISOCAST IOHS, trademark Octyldodecyl stearoyloxystearate: from Kokyu Alcohol Kogyo Co., Ltd., RISOCAST ODSHS, trademark Octyldodecanol: from Kokyu Alcohol Kogyo Co., Ltd., RISONOL 20SP, trademark Dextrin (palmitate/ethylhexanoate): from Chiba Flour Milling Co., Ltd., Rheopearl TT2, trademark, Inulin stearate: from Chiba Flour Milling Co., Ltd., Rheopearl ISL2, trademark, Glyceryl (behenate/eicosanedioate): from The Nisshin Oillio Group, Ltd., NOMCORT HK-G, trademark Di(C20-40)alkyl dimer-dilinoleate: from Koster Keunen Inc., Kester Wax K82-D, trademark Dibutyllauroylglutamide: from Ajinomoto Co., Inc., GP-1, trademark Stearyldimethicone: from Clariant, Silcare Silicone 41M65, trademark Amide terminated polyamide resin: from Arizona Chemical, Sylvaclear 200V, trademark Ester terminated polyamide resin: from Arizona Chemical, Uniclear 100VG, trademark Red No. 218: from KISHI KASEI CO., LTD., red No. 218
Red No. 226: from KISHI KASEI CO., LTD., red No. 226
Red No. 201: from KISHI KASEI CO., LTD., red No. 201
Red No. 202: from KISHI KASEI CO., LTD., red No. 202

Carmine: from Merk & Co., Inc., COLORONA CARMINE RED, trademark

Titanium oxide: from Ishihara Sangyo Kaisha, Ltd., Tipaque CR-30, trademark

Synthetic Fluorphlogopite, titanium oxide, iron oxide (lame agent): from Topy Industries, Ltd., Prominence RYH, trademark Borosilicic acid (Ca/Al), silica, titanium oxide, stannous oxide (lame agent): from Merk & Co., Inc., Ronastar Silver, trademark (PET/polymethylmethacrylate) laminate (lame agent): from Daiya Chemco, Ilidescent Glitter IF8101, trademark Trimethylolpropane triethylhexanoate: from Kokyu Alcohol Kogyo Co., Ltd., KAK TTO, trademark Isotridecyl isononanoate: from Kokyu Alcohol Kogyo Co., Ltd., KAK 139, trademark Hydrogenated castor oil isostearate, from Kokyu Alcohol Kogyo Co., Ltd., RISOCAST MIS, trademark Glyceryl tri(caprylate/caprate): from Kokyu Alcohol Kogyo Co., Ltd., TCG-M, trademark Isostearyl neopentanoate: from Kokyu Alcohol Kogyo Co., Ltd., NEOLIGHT 180P, trademark Neopentylglycol dicaprate: from Kokyu Alcohol Kogyo Co., Ltd., NPDC, trademark Candelilla wax: from STRAHL & PITSCH Inc., CANDELILLA WAX 75, trademark Beeswax: from Miki Kagaku Kogyo, beeswax Ceresin: from STRAHL & PITSCH Inc., Ceresin SP1020, trademark Polyethylene: from Baker Petrolite, Polywax 500, trademark Synthetic wax, (ethylene/propylene) copolymer: from Nihon Natural Products, LIPWAX PZ80-20, trademark Yellow No. 4 Aluminum Lake: from KISHI KASEI CO., LTD., Yellow No. 4 Aluminum Lake Bengara: from US Cosmetic Corporation, NHS-R-77491, trademark Blue No. 1 Aluminum Lake: from KISHI KASEI CO., LTD., Blue No. 1 Aluminum Lake Component (B):

Hydroxyethyl cellulose: from Sumitomo Seika Chemicals Co., Ltd., HEC, trademark

Hydroxypropylmethyl cellulose: from Shin-Etsu Chemical Co., Ltd., Metolose 60SH-4000, trademark (Acryloyldimethyltaurine ammonium/VP) copolymer: from Clariant, Aristoflex AVC, trademark Pentylene glycol: from Kokyu Alcohol Kogyo Co., Ltd., DIOL PD, trademark Polyquatanium-7: from Lion Corporation, Lipoflow MN, trademark Silk hydrolysate: from Seiwa Kasei Co., Ltd., Promois silk-1000Q, trademark Glycerin: from Kokyu Alcohol Kogyo Co., Ltd., TRIOL VE, trademark Carbomer, from Nikko Chemicals Co., Ltd., Carbopol ETD2050, trademark 1,3-butylene glycol: from Kokyu Alcohol Kogyo Co., Ltd., HAISUGARCANE BG, trademark Component (C):

Highly polymerized methyl polysiloxane (1): from Dow Corning Toray Co., Ltd., BY 22-029, trademark Storage stability, applicability, oily feeling, moisturizing ability, gloss, gloss-holding ability and safety to the skin in each of the cosmetics prepared in the Examples and the Comparative Examples were determined as follows:

Storage Stability

Water-in-oil type emulsified cosmetics, hair treatments, foundations, eye shadows, lip glosses and lipsticks, as indicated in the Examples and the Comparative Examples were prepared in accordance with the predetermined process. Three samples were prepared per each Example. Then, two of the samples were stored in a temperature-controlled bath, one at 25 degrees C. and the other at 45 degrees C., for one month. Remaining one of the samples was maintained successively at −10 degrees C., 25 degrees C. and 45 degrees C., each for 8 hours and then successively at 45 degrees C., 25 degrees C. and −10 degrees C., each for 8 hours in a temperature-controlled room. It took 48 hours per one operation. This sequential operation was repeated 5 times. The samples thus obtained were observed in respect to deterioration of appearance (occurrence of bulky particles), coloration, smelliness and separation by organoleptic assessments. As a result, in all samples, no deterioration of appearance, no coloration and no smelliness were observed. Therefore, the evaluation of storage stability was carried out only with regard to separation. Each sample was observed by eyes, and then, when there was no separation in all samples, the cosmetic was rated as "G". When the sample at one of the temperatures showed separation even if it was slight, the cosmetic was rated as "M". When the samples at two or more of the temperatures showed separation, even if it was slight, the cosmetic was rated as "B".

Applicability

After each of the cosmetics obtained in the Examples and the Comparative Examples, hair treatments, foundations, eye shadows, lip glosses and lipsticks, was applied to the skin, "applicability" was evaluated by twenty panels. For hair treatments, 2.0 g of each cosmetic were applied to the hair. For foundations, 1.0 g was applied to the face. For eye shadows, 0.1 g was applied to the eyelids. For lip glosses and lipsticks, 0.2 g was applied to the lips. The indication of the evaluation results is as follows. When not less than 15 panels among 20 panels evaluated the cosmetic as "good applicability", it was rated as "G". When from 6 to 9 panels evaluated the cosmetic as "good applicability", it was rated as "M". When not more than five panels evaluated the cosmetic as "good applicability", it was rated as "B".

Oily Feeling, Moisturizing Ability or Emollient Ability

After each of the cosmetics obtained in the Examples and the Comparative Examples, hair treatments, foundations, eye shadows, lip glosses and lipsticks, was applied to the skin, "oily feeling, moisturizing ability or emollient ability" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "proper oily feeling and moisturizing ability or emollient ability", it was rated as "G". When from 6 to 9 panels evaluated the cosmetic as "proper oily feeling and moisturizing ability or emollient ability", it was rated as "M". When not more than five panels evaluated the cosmetic as "proper oily feeling and moisturizing ability or emollient ability", it was rated as "B".

Gloss

After each of the cosmetics obtained in the Examples and the Comparative Examples, hair treatments, foundations, eye shadows, lip glosses and lipsticks, was applied to the skin, "gloss" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "good gloss", it was rated as "G". When from 6 to 9 panels evaluated the cosmetic as "good gloss", it was rated as "M". When not less than five panels evaluated the cosmetic as "good gloss", it was rated as "B".

Gloss-Holding Ability

After each of the cosmetics obtained in the Examples and the Comparative Examples, hair treatments, foundations, eye shadows, lip glosses and lipsticks, was applied to the skin, "gloss-holding ability" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "good gloss-holding ability", it was rated as "G". When from 6 to 9 panels evaluated the cosmetic as "good gloss-holding ability", it was rated as "M". When not less than five panels evaluated the cosmetic as "good gloss-holding ability", it was rated as "B".

Safety to the Skin

Subjects were twenty people, i.e. ten males and ten females. 0.05 g of each cosmetic obtained in the Examples or the Comparative Examples was applied to a circular patch with cotton lint of 1.0 cm diameter, which patch was applied to the forearm flexor of each subject and left for 24 hours. The patch was removed and the skin was examined 1 hour later and 24 hours later to rate the skin conditions of each subject according to the following criteria. When the results 1 hour later and 24 hours later were different, the stronger response was used for rating. When the 20 subjects exhibited (−), the rating was "G", when 1 to 2 subjects exhibited (+−) and the other subjects exhibited (−), the rating was "M"; and when three or more subjects exhibited (+−) and the other subjects exhibited (−) or when one or more subjects exhibited (+) to (+++), the rating was "B". For a hair treatment, aqueous 0.5% solution was used.

| Rating Criteria | |
|---|---|
| Skin Conditions | Rating |
| Erythema, edema, and blister | (+++) |
| Erythema and edema | (++) |
| Erythema | (+) |
| Slight erythema | (+−) |
| No erythema and no edema | (−) |

Examples 1 to 3

Hair Treatment

Each of the compositions (A) and (B) indicated in Table 2 was separately dissolved homogenously at a temperature of 75 to 80 degrees C. Next, Composition (B) was added to Composition (A) under stirring and then emulsified with a homomixer. Then, Component (C) was added to the emulsified product under stirring to obtain a mixture. The mixture thus obtained was then cooled to 30 degrees C. under further stirring to prepare a hair treatment. The evaluation results are shown in Table 2. Units of all figures indicated in Table 2 and in the following tables, Table 3 to 8, are % by mass.

TABLE 2

| Hair Treatment | | | | |
|---|---|---|---|---|
| Ingredient | | Ex. 1 | Ex. 2 | Ex. 3 |
| (A) | Hydroxyl compound obtained in Prep. Ex. 3 | 1.50 | 1.00 | 0.80 |
| | Dipentaerythrityl hexa(hydroxy-stearate/stearate/rosinate) | — | 1.00 | — |
| | (Polyglyceryl-2 isostearate/dimer dilinoleic acid) copolymer | — | — | 2.00 |
| | Bis-ethoxydiglycol succinate | 5.00 | — | — |
| | Neopentylglycol diisononanoate | 2.00 | 4.00 | — |
| | Isopropyl palmitate | — | — | 2.00 |
| | Jojoba oil | 1.00 | — | — |
| | Macadamia nut oil | — | 1.00 | — |
| | Stearyl alcohol | 9.00 | — | 6.00 |
| | Cetostearyl alcohol | — | 9.00 | — |
| | Behenyl alcohol | — | — | 2.00 |
| | Dipropylene glycol | 4.00 | 3.00 | 3.00 |
| | Stearyl trimonium chloride | 1.00 | — | 1.00 |
| | Distearyl dimonium chloride | — | 1.00 | 1.00 |
| | Behen trimonium chloride | — | 0.50 | — |
| | Dicoco dimonium chloride | — | 1.00 | — |
| | Amodimethicone | 0.50 | — | 0.20 |

TABLE 2-continued

| Hair Treatment | | | | |
|---|---|---|---|---|
| | Ingredient | Ex. 1 | Ex. 2 | Ex. 3 |
| | Cyclomethicone | — | 1.00 | — |
| | Dimethicone | 1.00 | 2.00 | 3.00 |
| | Phenoxy ethanol | — | 0.10 | — |
| (B) | Hydroxyethyl cellulose | 0.30 | — | 0.30 |
| | Hydroxypropyl methyl cellulose | — | 0.20 | — |
| | (Acryloyldimethyltaurine ammonium/VP)copolymer | — | 0.20 | — |
| | Pentylene glycol | 3.00 | — | — |
| | Polyquatanium-7 | — | 1.00 | — |
| | Silk hydrolysate | 0.01 | — | 0.02 |
| | Glycolic acid | 1.00 | — | 1.00 |
| | Methyl paraben | — | — | 0.20 |
| | Purified water | 69.29 | 74.00 | 76.48 |
| (C) | Highly polymerized methyl polysiloxane (1) | 1.40 | — | 1.00 |
| | Total | 100.00 | 100.00 | 100.00 |
| | Storage stability | G | G | G |
| | Applicability | G | G | G |
| | Oily feeling and moisturizing ability (or emollient ability) | G | G | G |
| | Gloss | G | G | G |
| | Gloss-holding ability | G | G | G |
| | Safety to the skin | G | G | G |

Comparative Examples 1 to 5

Hair Treatment

The procedures of Example 1 were repeated, except that the hydroxyl compounds obtained in Comparative Preparation Examples 1, 2, 3, 7 and 8 were used respectively, in place of the hydroxyl compound obtained in Preparation Example 3. The evaluation results are shown in Table 3.

TABLE 3

| Hair Treatment | | | | | | |
|---|---|---|---|---|---|---|
| | Ingredient | Com. Ex. 1 | Com. Ex. 2 | Com. Ex. 3 | Com. Ex. 4 | Com. Ex. 5 |
| (A) | Hydroxyl compound obtained in Com. Prep. Ex. 1 | 1.50 | — | — | — | — |
| | Hydroxyl compound obtained in Com. Prep. Ex. 2 | — | 1.50 | — | — | — |
| | Hydroxyl compound obtained in Com. Prep. Ex. 3 | — | — | 1.50 | — | — |
| | Hydroxyl compound obtained in Com. Prep. Ex. 7 | — | — | — | 1.50 | — |
| | Hydroxyl compound obtained in Com. Prep. Ex. 8 | — | — | — | — | 1.50 |
| | Dipentaerythrityl hexa(hydroxystearate/stearate/rosinate) | — | — | — | — | — |
| | (Polyglyceryl-2 isostearate/dimer dilinoleic acid) copolymer | — | — | — | — | — |
| | Bis-ethoxydiglycol succinate | 5.00 | 5.00 | 5.00 | 5.00 | 5.00 |
| | Neopentylglycol diisononanoate | 2.00 | 2.00 | 2.00 | 2.00 | 2.00 |
| | Isopropyl palmitate | — | — | — | — | — |
| | Jojoba oil | 1.00 | 1.00 | 1.00 | 1.00 | 1.00 |
| | Macadamia nut oil | — | — | — | — | — |
| | Stearyl alcohol | 9.00 | 9.00 | 9.00 | 9.00 | 9.00 |
| | Cetostearyl alcohol | — | — | — | — | — |
| | Behenyl alcohol | — | — | — | — | — |
| | Dipropylene glycol | 4.00 | 4.00 | 4.00 | 4.00 | 4.00 |
| | Stearyl trimonium chloride | 1.00 | 1.00 | 1.00 | 1.00 | 1.00 |
| | Distearyl dimonium chloride | — | — | — | — | — |
| | Behen trimonium chloride | — | — | — | — | — |
| | Dicoco dimonium chloride | — | — | — | — | — |
| | Amodimethicone | 0.50 | 0.50 | 0.50 | 0.50 | 0.50 |
| | Cyclomethicone | — | — | — | — | — |
| | Dimethicone | 1.00 | 1.00 | 1.00 | 1.00 | 1.00 |
| | Phenoxy ethanol | — | — | — | — | — |
| (B) | Hydroxyethyl cellulose | 0.30 | 0.30 | 0.30 | 0.30 | 0.30 |
| | Hydroxypropylmethyl cellulose | — | — | — | — | — |
| | (Acryloyldimethyltaurine ammonium/VP)copolymer | — | — | — | — | — |
| | Pentylene glycol | 3.00 | 3.00 | 3.00 | 3.00 | 3.00 |
| | Polyquatanium-7 | — | — | — | — | — |
| | Silk hydrolysate | 0.01 | 0.01 | 0.01 | 0.01 | 0.01 |
| | Glycolic acid | 1.00 | 1.00 | 1.00 | 1.00 | 1.00 |
| | Methyl paraben | — | — | — | — | — |
| | Purified water | 69.29 | 69.29 | 69.29 | 69.29 | 69.29 |
| (C) | Highly polymerized methyl polysiloxane (1) | 1.40 | 1.40 | 1.40 | 1.40 | 1.40 |
| | Total | 100.00 | 100.00 | 100.00 | 100.00 | 100.00 |
| | Storage stability | M | M | M | B | B |
| | Applicability | B | M | M | M | G |
| | Oily feeling and moisturizing ability (or emollient ability) | B | B | B | B | G |
| | Gloss | G | G | G | G | G |
| | Gloss-holding ability | B | M | G | G | B |
| | Safety to the skin | G | G | G | B | M |

In Examples 1 to 3, hair treatments were prepared using the hydroxyl compound obtained in Preparation Example 3 wherein the amount of the hydroxyl compound used was varied. All the cosmetics exhibited good properties. Meanwhile, in Comparative Examples 1 to 5, the hydroxyl compound obtained in Preparation Example 3 was changed to the hydroxyl compound obtained in Comparative Preparation Examples 1, 2, 3, 7 or 8, respectively, in order to compare each hydroxyl compound to that of Example 1. All the cosmetics exhibited poor properties.

Examples 4 to 6

Creamy Foundation

Each of the compositions (A) and (B) indicated in Table 4 was separately dissolved homogenously at a temperature of 75 to 80 degrees C. Next, Composition (B) was added to Composition (A) under stirring and then emulsified with a homomixer. The mixture thus obtained was then cooled to 30 degrees C. under stirring to prepare a creamy foundation. The evaluation results are shown in Table 4.

TABLE 4

Creamy Foundation (w/o type)

| | Ingredient | Ex. 4 | Ex. 5 | Ex. 6 |
|---|---|---|---|---|
| (A) | Hydroxyl compound obtained in Prep. Ex. 3 | 1.00 | 0.50 | 1.50 |
| | Hexyldecyl isostearate | 20.00 | — | — |
| | Neopentylglycol diethylhexanoate | — | 5.00 | 20.00 |
| | Squalane | 5.00 | — | 2.00 |
| | Cyclomethicone | — | 20.00 | 5.00 |
| | Dimethicone | — | 2.00 | — |
| | (Diglycerin/dilinoleic acid/hydroxystearic acid)copolymer | — | — | 1.50 |
| | Sorbitan monoisostearate | 1.00 | — | 1.00 |
| | Dimethicone copolyol | — | 1.20 | — |
| | Dipropylene glycol | 3.00 | — | 5.00 |
| | Pentylene glycol | 2.00 | 2.00 | — |
| | Cetanol | 2.00 | 2.00 | — |
| | Cetostearyl alcohol | — | 1.00 | — |
| | Hydrogenated rapeseed oil alcohol | — | 0.50 | — |
| | Dextrin palmitate | 3.00 | 2.00 | 3.00 |
| | Microcrystalline wax | — | 4.00 | 3.00 |
| | Hydrophobicated titanium oxide | 8.00 | 7.00 | 7.50 |
| | Hydrophobicated iron oxide yellow | 1.20 | 1.20 | 1.25 |
| | Hydrophobicated iron oxide red | 0.30 | 0.30 | 0.28 |
| | Hydrophobicated iron oxide black | 0.15 | 0.15 | 0.18 |
| | Talc | 1.40 | 1.35 | 2.00 |
| | Ethylhexyl methoxycinnamate | 1.00 | 1.00 | 1.00 |
| | Nylon-8 | 0.50 | — | 0.20 |
| | Crosslinked type silicone powder | — | 2.00 | 1.00 |
| (B) | Glycerin | 2.00 | 3.00 | 2.00 |
| | Hydroxyethyl cellulose | — | 0.30 | — |
| | Carbomer | — | — | 0.40 |
| | Sodium hydroxide | — | — | 0.15 |
| | Preservative | proper amount | proper amount | proper amount |
| | Purified water | 48.45 | 43.50 | 42.04 |
| | Total | 100.00 | 100.00 | 100.00 |
| | Storage stability | G | G | G |
| | Applicability | G | G | G |
| | Oily feeling and moisturizing ability (or emollient ability) | G | G | G |
| | Gloss | G | G | G |
| | Gloss-holding ability | G | G | G |
| | Safety to the skin | G | G | G |

Examples 7 to 8

Eye Shadow

Each of the compositions (A) and (B) indicated in Table 5 was separately dissolved homogenously at a temperature of 75 to 80 degrees C. Next, Composition (B) was added to Composition (A) under stirring and then emulsified with a homomixer. The mixture thus obtained was then cooled to 30 degrees C. under stirring to prepare an eye shadow. The evaluation results are shown in Table 5.

TABLE 5

Eye Shadow

| | Ingredient | Ex. 7 | Ex. 8 |
|---|---|---|---|
| (A) | Hydroxyl compound obtained in Prep. Ex. 3 | 2.50 | 2.00 |
| | Neopentylglycol diethylhexanoate | 8.00 | 7.00 |
| | Isostearyl isostearate | — | 1.00 |
| | Triethylhexanoin | — | 1.00 |
| | Mineral oil | 2.00 | — |
| | Diisostearyl malate | 5.00 | — |
| | Glyceryl stearate (SE) | 1.50 | — |
| | Polyglyceryl-10 stearate | 1.00 | — |
| | Sorbitan monoisostearate | — | 1.00 |
| | Dextrin palmitate | 3.00 | 3.00 |
| | Hydrophobicated ultramarine | 8.20 | 8.20 |
| | Hydrophobicated iron oxide black | 1.10 | 1.10 |
| | TiO2 coated mica | 1.00 | 1.00 |
| | Cyclomethicone | 5.00 | 8.00 |
| (B) | Glycerin | 2.00 | 1.50 |
| | 1,3-Butylene glycol | 2.00 | 1.50 |
| | Pentylene glycol | 3.00 | 3.00 |
| | Preservative | proper amount | proper amount |
| | Purified water | 54.70 | 60.70 |
| | Total | 100.00 | 100.00 |
| | Storage stability | G | G |
| | Applicability | G | G |
| | Oily feeling and moisturizing ability (or emollient ability) | G | G |
| | Gloss | G | G |
| | Gloss-holding ability | G | G |
| | Safety to the skin | G | G |

Examples 9 to 12

Lip Gloss

Ingredients indicated in Table 6 were dissolved homogenously at 110 degrees C., and then defoamed. Then, the mixture thus obtained was cooled to 30 degrees C. to prepare a lip gloss. The evaluation results are shown in Table 6.

TABLE 6

Lip Gloss

| Ingredient | Ex. 9 | Ex. 10 | Ex. 11 | Ex. 12 |
|---|---|---|---|---|
| Hydroxyl compound obtained in Prep. Ex. 3 | 40.00 | 10.00 | 30.00 | 50.00 |
| Hydrogenated polyisobutene | — | 35.00 | — | — |
| Hydrogenated castor oil dimer-dilinoleate | — | — | 1.00 | — |
| (Diglycerin/dilinoleic acid/hydroxystearic acid)copolymer | — | — | 1.00 | — |
| Polyglyceryl-2 diisostearate | 25.00 | — | 15.00 | — |
| Polyglyceryl-2 triisostearate | — | 20.00 | 5.00 | 5.00 |
| Diisostearyl malate | 15.00 | 10.00 | 20.00 | 5.00 |
| Pentaerythrityl tetraisostearate | 10.00 | — | 10.00 | 8.40 |

TABLE 6-continued

Lip Gloss

| Ingredient | Ex. 9 | Ex. 10 | Ex. 11 | Ex. 12 |
|---|---|---|---|---|
| Ethylhexyl hydroxystearate | 1.70 | 3.00 | — | 15.00 |
| Octyldodecyl stearoyloxystearate | — | 10.02 | 11.80 | — |
| Squalane | — | 5.00 | — | — |
| Jojoba oil | — | 3.00 | — | — |
| Octyldodecanol | — | — | 5.00 | 10.00 |
| Dextrin (palmitate/ethylhexanoate) | 4.00 | 2.00 | — | — |
| Inulin stearate | — | — | — | 2.00 |
| Glyceryl (behenate/eicosanedioate) | — | — | — | 2.00 |
| Di(C20-40)alkyl dimer-dilinoleate | 3.00 | — | — | — |
| Dibutyllauroylglutamide | — | — | 0.50 | — |
| Stearyldimethicone | — | 1.50 | — | — |
| Amide terminated polyamide resin | — | — | — | 0.50 |
| Ester terminated polyamide resin | — | — | — | 0.60 |
| Red No. 218 | — | — | — | 0.30 |
| Red No. 226 | 0.30 | — | — | — |
| Red No. 201 | — | 0.01 | — | — |
| Red No. 202 | — | 0.02 | — | — |
| Carmine | — | — | 0.30 | — |
| Titanium oxide | — | 0.15 | — | — |
| TiO2 coated mica (pearlescent agent) | 1.00 | — | — | 0.50 |
| Synthetic Fluorphlogopite, titanium oxide, iron oxide (lame agent) | — | 0.30 | — | — |
| Borosilicic acid(Ca/Al), silica, titanium oxide, stannous oxide (lame agent) | — | — | 0.40 | — |
| (PET/polymethylmethacrylate) laminate (lame agent) | — | — | — | 0.50 |
| Total | 100.00 | 100.00 | 100.00 | 100.00 |
| Storage stability | G | G | G | G |
| Applicability | G | G | G | G |
| Oily feeling and moisturizing ability (or emollient ability) | G | G | G | G |
| Gloss | G | G | G | G |
| Gloss-holding ability | G | G | G | G |
| Safety to the skin | G | G | G | G |

Comparative Examples 6 to 12

Lip Gloss

The procedures of Example 9 were repeated, except that the hydroxyl compounds obtained in Comparative Preparation Examples 1 to 3, and 5 to 8 were used respectively, in place of the hydroxyl compound obtained in Preparation Example 3. The evaluation results are shown in Table 7.

TABLE 7

Lip Gloss

| Ingredient | Com. Ex. 6 | Com. Ex. 7 | Com. Ex. 8 | Com. Ex. 9 | Com. Ex. 10 | Com. Ex. 11 | Com. Ex. 12 |
|---|---|---|---|---|---|---|---|
| Hydroxyl compound obtained in Com. Prep. Ex. 1 | 40.00 | — | — | — | — | — | — |
| Hydroxyl compound obtained in Com. Prep. Ex. 2 | — | 40.00 | — | — | — | — | — |
| Hydroxyl compound obtained in Com. Prep. Ex. 3 | — | — | 40.00 | — | — | — | — |
| Hydroxyl compound obtained in Com. Prep. Ex. 5 | — | — | — | 40.00 | — | — | — |
| Hydroxyl compound obtained in Com. Prep. Ex. 6 | — | — | — | — | 40.00 | — | — |
| Hydroxyl compound obtained in Com. Prep. Ex. 7 | — | — | — | — | — | 40.00 | — |
| Hydroxyl compound obtained in Com. Prep. Ex. 8 | — | — | — | — | — | — | 40.00 |
| Hydrogenated castor oil dimer-dilinoleate | — | — | — | — | — | — | — |
| (Diglycerin/dilinoleic acid/hydroxystearic acid)copolymer | — | — | — | — | — | — | — |
| Polyglyceryl-2 diisostearate | 25.00 | 25.00 | 25.00 | 25.00 | 25.00 | 25.00 | 25.00 |
| Polyglyceryl-2 triisostearate | — | — | — | — | — | — | — |
| Diisostearyl malate | 15.00 | 15.00 | 15.00 | 15.00 | 15.00 | 15.00 | 15.00 |
| Pentaerythrityl tetraisostearate | 10.00 | 10.00 | 10.00 | 10.00 | 10.00 | 10.00 | 10.00 |
| Ethylhexyl hydroxystearate | 1.70 | 1.70 | 1.70 | 1.70 | 1.70 | 1.70 | 1.70 |
| Octyldodecyl stearoyloxystearate | — | — | — | — | — | — | — |
| Squalane | — | — | — | — | — | — | — |
| Jojoba oil | — | — | — | — | — | — | — |
| Octyldodecanol | — | — | — | — | — | — | — |
| Dextrin (palmitate/ethylhexanoate) | 4.00 | 4.00 | 4.00 | 4.00 | 4.00 | 4.00 | 4.00 |
| Inulin stearate | — | — | — | — | — | — | — |
| Glyceryl (behenate/eicosanedioate) | — | — | — | — | — | — | — |
| Di(C20-40)alkyl dimer-dilinoleate | 3.00 | 3.00 | 3.00 | 3.00 | 3.00 | 3.00 | 3.00 |
| Dibutyllauroylglutamide | — | — | — | — | — | — | — |
| Stearyldimethicone | — | — | — | — | — | — | — |
| Amide terminated polyamide resin | — | — | — | — | — | — | — |
| Ester terminated polyamide resin | — | — | — | — | — | — | — |
| Red No. 218 | — | — | — | — | — | — | — |
| Red No. 226 | 0.30 | 0.30 | 0.30 | 0.30 | 0.30 | 0.30 | 0.30 |
| Red No. 201 | — | — | — | — | — | — | — |
| Red No. 202 | — | — | — | — | — | — | — |
| Carmine | — | — | — | — | — | — | — |
| Titanium oxide | — | — | — | — | — | — | — |
| TiO2 coated mica (pearlescent agent) | 1.00 | 1.00 | 1.00 | 1.00 | 1.00 | 1.00 | 1.00 |
| Synthetic Fluorphlogopite, titanium oxide, iron oxide (lame agent) | — | — | — | — | — | — | — |

TABLE 7-continued

| Ingredient | Com. Ex. 6 | Com. Ex. 7 | Com. Ex. 8 | Com. Ex. 9 | Com. Ex. 10 | Com. Ex. 11 | Com. Ex. 12 |
|---|---|---|---|---|---|---|---|
| Lip Gloss | | | | | | | |
| Borosilicic acid(Ca/Al), silica, titanium oxide, stamous oxide (lame agent) | — | — | — | — | — | — | — |
| PET/polymethylmethacrylate) laminate (lame agent) | — | — | — | — | — | — | — |
| Total | 100.00 | 100.00 | 100.00 | 100.00 | 100.00 | 100.00 | 100.00 |
| Storage stability | G | G | G | G | G | G | G |
| Applicability | G | G | G | G | G | G | G |
| Oily feeling and moisturizing ability (or emollient ability) | G | G | G | G | G | G | G |
| Gloss | G | G | G | G | G | G | G |
| Gloss-holding ability | B | B | B | B | B | B | B |
| Safety to the skin | G | G | G | G | G | B | M |

In Examples 9 to 12, lip glosses were prepared using the hydroxyl compound obtained in Preparation Example 3, wherein the amount of the hydroxyl compound used was varied. All the cosmetics exhibited good properties. Meanwhile, use was made of the hydroxyl compounds obtained in Comparative Preparation Examples 1 to 3 in Comparative Examples 6 to 8, respectively, and of the hydroxyl compounds obtained in Preparation Examples 5 to 8 in Comparative Examples 9 to 12, respectively, in place of the hydroxyl compound obtained in Preparation Example 3 used in Example 9. All the cosmetics exhibited poor gloss-holding ability.

Examples 13 to 14

Palette Type Lip Gloss

Ingredients indicated in Table 8 were dissolved homogenously at 110 degrees C., and then defoamed. Then, the mixture thus obtained was poured into a proper mold, and cooled to 30 degrees C. to prepare a lip gloss. The evaluation results are shown in Table 8.

TABLE 8

| Ingredient | Ex. 13 | Ex. 14 |
|---|---|---|
| Palette Type Lip Gloss | | |
| Hydroxyl compound obtained in Prep. Ex. 3 | 20.00 | 35.00 |
| Hydrogenated polyisobutene | 20.00 | — |
| Hydrogenated castor oil dimer-dilinoleate | — | 5.00 |
| (Diglycerin/dilinoleic acid/hydroxystearic acid)copolymer | — | 1.00 |
| Polyglyceryl-2 diisostearate | 30.00 | 15.00 |
| Polyglyceryl-2 triisostearate | — | 15.00 |
| Diisostearyl malate | 5.00 | 10.84 |
| Pentaerythrityl tetraisostearate | 10.00 | — |
| Trimethylolpropane triethylhexanoate | — | 3.00 |
| Ethylhexyl hydroxystearate | — | 2.00 |
| Isotridecyl isononanoate | — | 5.00 |
| Octyldodecyl stearoyloxystearate | 9.25 | — |
| Squalane | — | 1.00 |
| Jojoba oil | — | 1.00 |
| Octyldodecanol | — | 1.00 |
| Dextrin (palmitate/ethylhexanoate) | — | 1.50 |
| Inulin stearate | — | 1.00 |
| Dibutyllauroylglutamide | — | 1.50 |
| Amide terminated polyamide resin | 2.00 | — |
| Ester terminated polyamide resin | 3.00 | — |
| Red No. 218 | 0.10 | — |
| Red No. 226 | 0.20 | — |
| Red No. 201 | — | 0.02 |
| Red No. 202 | — | 0.01 |
| Carmine | 0.05 | — |
| Titanium oxide | — | 0.13 |
| TiO2 coated mica (pearlescent agent) | — | 1.00 |
| Synthetic Fluorphlogopite, titanium oxide, iron oxide (lame agent) | 0.10 | — |
| Borosilicic acid(Ca/Al), silica, titanium oxide, stannous oxide (lame agent) | 0.10 | — |
| (PET/polymethylmethacrylate) laminate (lame agent) | 0.20 | — |
| Total | 100.00 | 100.00 |
| Storage stability | G | G |
| Applicability | G | G |
| Oily feeling and moisturizing ability (or emollient ability) | G | G |
| Gloss | G | G |
| Gloss-holding ability | G | G |
| Safety to the skin | G | G |

Examples 15 to 18

Lipstick

Ingredients indicated in Table 9 were dissolved homogenously at 110 degrees C., and then defoamed. Then, the mixture thus obtained was poured into a proper mold, and cooled at 10 degrees C. for 20 minutes to prepare a lipstick. The evaluation results are shown in Table 9.

TABLE 9

| Ingredient | Ex. 15 | Ex. 16 | Ex. 17 | Ex. 18 |
|---|---|---|---|---|
| Lipstick | | | | |
| Hydroxyl compound obtained in Prep. Ex. 3 | 5.00 | 15.00 | 25.00 | 30.00 |
| Hydrogenated polyisobutene | 5.00 | — | — | — |
| Hydrogenated castor oil dimer-dilinoleate | 10.00 | 6.00 | — | — |
| Dipentaerythrityl hexa(hydroxysteate/stearate/rosinate) | — | 11.00 | — | — |
| Hydrogenated castor oil isostearate | — | — | 6.00 | — |
| Polyglyceryl-2 diisostearate | — | 5.00 | 5.00 | — |
| Polyglyceryl-2 triisostearate | 6.00 | — | 10.00 | — |
| Diisostearyl malate | 10.00 | 14.00 | — | — |
| Pentaerythrityl tetraisostearate | — | 8.00 | 10.00 | 15.00 |
| Glyceryl tri(caprylate/caprate) | 20.00 | 14.30 | 8.70 | — |
| Ethylhexyl hydroxystearate | — | 9.70 | 2.00 | 10.00 |

TABLE 9-continued

Lipstick

| Ingredient | Ex. 15 | Ex. 16 | Ex. 17 | Ex. 18 |
|---|---|---|---|---|
| Isostearyl neopentanoate | 15.00 | — | 10.00 | — |
| Neopentylglycol dicaprate | — | — | 5.00 | 10.74 |
| Squalane | 1.00 | — | — | 5.00 |
| Octyldodecanol | 5.00 | — | — | 6.00 |
| Dextrin palmitate | — | 1.50 | — | — |
| Candelilla wax | 3.00 | — | 2.00 | — |
| Beeswax | — | 3.00 | 3.00 | — |
| Ceresin | 5.00 | — | 2.00 | 6.00 |
| Polyethylene | 5.00 | 3.00 | 3.00 | 5.00 |
| Synthetic wax, (ethylene/propylene)copolymer | — | 4.00 | 3.00 | 1.00 |
| Microcrystalline wax | 3.00 | 3.00 | 3.00 | 4.00 |
| Yellow No. 4 Aluminum Lake | — | — | — | — |
| Red No. 201 | 1.40 | — | — | — |
| Red No. 202 | 1.10 | 2.00 | 1.60 | — |
| Bengara | 1.20 | — | — | 0.36 |
| Red No. 226 | — | — | — | 1.60 |
| Blue No. 1 Aluminum Lake | — | — | 0.10 | — |
| Titanium oxide | 0.80 | — | 0.10 | 1.00 |
| TiO2 coated mica (pearlescent agent) | 2.50 | — | — | 4.00 |
| Synthetic Fluorphlogopite, titanium oxide, iron oxide (lame agent) | — | — | 0.10 | 0.30 |
| Borosilicic acid(Ca/Al), silica, titanium oxide, stannous oxide (lame agent) | — | — | — | — |
| PET/polymethylmethacrylate) laminate (lame agent) | — | — | 0.40 | — |
| Total | 100.00 | 99.50 | 100.00 | 100.00 |
| Storage stability | G | G | G | G |
| Applicability | G | G | G | G |
| Oily feeling and moisturizing ability (or emollient ability) | G | G | G | G |
| Gloss | G | G | G | G |
| Gloss-holding ability | G | G | G | G |
| Safety to the skin | G | G | G | G |

The present hydroxyl compound has gloss-holding ability which have not been attained by any prior art hydroxyl compounds. That is, the excellent gloss is maintained even if the hydroxyl compound comes into contact with moisture or humidity in air or with saliva. Accordingly, the hydroxyl compound of the present invention is useful for cosmetics such as hair treatments, foundations, and eye shadows. Among others, it is useful for lipsticks or lip glosses, of which gloss tends to easily disappear upon contact with saliva.

The invention claimed is:

1. A hydroxyl compound obtained by a process comprising, reacting a di- or higher-valent alcohol with a monovalent carboxylic acid to obtain an ester compound, and then reacting the ester compound with dimer acid, the di- or higher-valent alcohol comprising diglycerin, and the monovalent carboxylic acid comprising a carboxylic acid having 5 to 10 carbon atoms, and a molar ratio among diglycerin, the carboxylic acid having 5 to 10 carbon atoms and dimer acid being 1.0:1.5 to 1.6:0.4 to 0.6.

2. The hydroxyl compound according to claim 1, wherein the monovalent carboxylic acid comprises a carboxylic acid having 9 to 10 carbon atoms.

3. The hydroxyl compound according to claim 1, wherein the monovalent carboxylic acid comprises isononanoic acid.

4. The hydroxyl compound according to claim 1, wherein the molar ratio among diglycerin, the carboxylic acid having 5 to 10 carbon atoms and dimer acid is 1.0:1.5 to 1.6:0.5 to 0.6.

5. The hydroxyl compound according to claim 1, wherein a hydroxyl value of the hydroxyl compound is in a range of 90 to 160.

6. The hydroxyl compound according to claim 1, wherein a hydroxyl value of the hydroxyl compound is in a range of 100 to 150.

7. The hydroxyl compound according to claim 1, wherein a viscosity at 60 degrees C. of the hydroxyl compound is in a range of 900 to 3,000 Pa·s.

8. The hydroxyl compound according to claim 1, wherein a viscosity at 60 degrees C. of the hydroxyl compound is in a range of 1,000 to 2,600 Pa·s.

9. The hydroxyl compound according to claim 1, wherein a number average molecular weight of the hydroxyl compound is in a range of 700 to 5,000.

10. The hydroxyl compound according to claim 1, wherein a number average molecular weight of the hydroxyl compound is in a range of 720 to 4,400.

11. The hydroxyl compound according to claim 1, wherein water-holding property of the hydroxyl compound is in a range of 30 to 100%.

12. The hydroxyl compound according to claim 1, wherein water-holding property of the hydroxyl compound is in a range of 40 to 90%.

13. A cosmetic comprising the hydroxyl compound according to claim 1.

14. A cosmetic comprising the hydroxyl compound according to claim 1 in an amount of 0.1 to 80% by mass.

15. A cosmetic comprising the hydroxyl compound according to claim 1 in an amount of 0.5 to 70% by mass.

16. A hair treatment, a foundation, an eye shadow, a lip gloss or a lipstick comprising the hydroxyl compound according to claim 1.

* * * * *